(12) United States Patent
Morita et al.

(10) Patent No.: US 7,655,677 B2
(45) Date of Patent: Feb. 2, 2010

(54) COMPOSITION AND METHOD FOR CONTROLLING HOUSE INSECT PEST

(75) Inventors: Masayuki Morita, Shiga (JP); Osamu Imai, Shiga (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 38 days.

(21) Appl. No.: 12/105,779

(22) Filed: Apr. 18, 2008

(65) Prior Publication Data

US 2008/0200522 A1 Aug. 21, 2008

Related U.S. Application Data

(63) Continuation of application No. 10/504,158, filed as application No. PCT/JP03/01711 on Feb. 18, 2003, now abandoned.

(30) Foreign Application Priority Data

Feb. 22, 2002 (JP) .............................. 2002-045837
Aug. 2, 2002 (JP) .............................. 2002-226478

(51) Int. Cl.
*A01N 43/40* (2006.01)
*A01N 53/02* (2006.01)
*A01P 17/00* (2006.01)

(52) U.S. Cl. ...................... 514/351; 514/341; 514/531; 514/594; 514/596

(58) Field of Classification Search ................. 514/351, 514/341, 531, 594, 596
See application file for complete search history.

(56) References Cited

U.S. PATENT DOCUMENTS

| 5,360,806 | A | | 11/1994 | Toki et al. |
| 5,747,519 | A | * | 5/1998 | Kodama et al. ............. 514/407 |
| 5,921,018 | A | * | 7/1999 | Hirose et al. ................ 43/132.1 |
| 5,990,043 | A | * | 11/1999 | Kugler et al. ................ 504/150 |
| 7,195,773 | B2 | | 3/2007 | Morita et al. |
| 2007/0142439 | A1 | | 6/2007 | Morita et al. |

FOREIGN PATENT DOCUMENTS

WO WO 9324011 A1 * 12/1993

OTHER PUBLICATIONS

Taiwanese Office Action dated Mar. 4, 2008 (w/Partial Translation).

* cited by examiner

*Primary Examiner*—John Pak
*Assistant Examiner*—Andriae M Holt
(74) *Attorney, Agent, or Firm*—Oblon, Spivak, McClelland, Maier & Neustadt, L.L.P.

(57) ABSTRACT

The present invention provides a composition for controlling a house insect pest, such as termites, ants or cockroaches, which comprises, as active ingredients, at least two compounds selected from the group consisting of (a) a certain pyridine compound, (b) a benzoylurea compound, (c) a pyrethroid compound and (d) a certain hydrazone compound; and a composition for controlling a house insect pest, which comprises, as an active ingredient, a certain hydrazone compound.

7 Claims, No Drawings

COMPOSITION AND METHOD FOR CONTROLLING HOUSE INSECT PEST

This application is a Continuation of U.S. application Ser. No. 10/504,158, filed on May 16, 2005, now abandoned, which was filed as a 371 of International Application PCT/JP03/01711, filed on Feb. 18, 2003.

TECHNICAL FIELD

The present invention relates to a composition for controlling a house insect pest, which comprises, as active ingredients, at least two compounds selected from the group consisting of (a) a certain specific pyridine compound or its salt, (b) a benzoylurea compound, (c) a pyrethroid compound and (d) a certain specific hydrazone compound or its salt, particularly to a composition for controlling termites, ants or cockroaches. Further, it relates also to a composition for controlling a house insect pest, which comprises, as an active ingredient, the above hydrazone compound or its salt.

BACKGROUND ART

Pyridine compounds may, for example, be those described in e.g. U.S. Pat. No. 5,360,806, WO98/57969 and WO 02/34050. Hydrazone compounds may be those described in U.S. Pat. No. 5,288,727 and Japanese patent 307192.

As conventional agents for controlling termites, organophosphorus compounds such as chlorpyrifos, or pyrethroids may, for example, be mentioned. Further, as agents for controlling ants, hydramethylnon, lithium sulfonate, organophosphorus compounds, carbamates, or pyrethroids, may, for example, be mentioned. Further, as agents for controlling cockroaches, pyrethroids or organophosphorus compounds, may, for example, be mentioned. However, among them, there are some which are feared to present toxicity against mammals or adverse effects to environment. Under the circumstances, a new agent for controlling a house insect pest is desired.

DISCLOSURE OF THE INVENTION

The present inventors have conducted an extensive research for an agent for controlling a house insect pest. As a result, they have found specifically that by combining at least two compounds selected from the group consisting of (a) certain specific pyridine compounds or salts thereof, (b) benzoylurea compounds, (c) pyrethroid compounds and (d) certain specific hydrazone compounds or salts thereof, as active ingredients, particularly excellent effects for controlling house insect pests can be expressed, and that certain hydrazone compounds or salts thereof have excellent effects for controlling house insect pests. The present invention has been accomplished on the basis of this discovery.

Namely, the present invention provides a composition for controlling a house insect pest, which comprises, as active ingredients, at least two compounds selected from the group consisting of (a) a pyridine compound of the formula (I) or its salt:

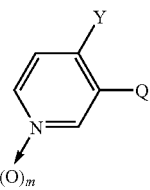

wherein Y is a haloalkyl group, m is 0 or 1, and Q is

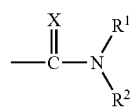

or a substituted or unsubstituted heterocyclic group, (wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, a —$C(W^1)R^3$ group, a —$OR^4$ group, a —$S(O)_nR^5$ group, a —$NHR^6$ group,

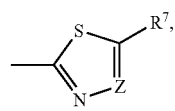

a —$C(R^8)$=NO—$R^9$ group or a substituted or unsubstituted aryl group, or $R^1$ and $R^2$ may form a =$C(R^{10})R^{11}$ group or may form a $C_4$-$C_5$ 5-membered or 6-membered heterocyclic group which may contain a nitrogen atom or an oxygen atom, together with an adjacent nitrogen atom, $R^3$ is a substituted or unsubstituted alkyl group, a substituted or unsubstituted alkenyl group, a substituted or unsubstituted alkynyl group, a substituted or unsubstituted cycloalkyl group, a substituted or unsubstituted aryl group, an alkoxy group, an alkylthio group or a mono- or dialkylamino group, $R^4$ is a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted aryl group, a substituted or unsubstituted heterocyclic group or a —$COR^3$ group, $R^5$ is an alkyl group or a dialkylamino group, $R^6$ is an alkyl group or an aryl group, Z is N or a —C—$R^7$ group, $R^7$ is a hydrogen atom, a halogen atom, a substituted or unsubstituted alkyl group, an alkoxy group, an alkylthio group or a nitro group, $R^8$ and $R^9$ are respectively independently a hydrogen atom, a substituted or unsubstituted alkyl group, a substituted or unsubstituted alkenyl group, a substituted or unsubstituted alkynyl group, a substituted or unsubstituted aryl group or a substituted or unsubstituted heterocyclic group, $R^{10}$ and $R^{11}$ are respectively independently a hydrogen atom, a substituted or unsubstituted alkyl group, a substituted or unsubstituted alkenyl group, a substituted or unsubstituted heterocyclic group, a —N—$(R^{12})R^{13}$ group, a substituted or unsubstituted alkoxy group, a substituted or unsubstituted alkylthio group, $R^{12}$ and $R^{13}$ are respectively independently a hydrogen atom, a substituted or unsubstituted alkyl group, a substituted or unsubstituted alkenyl group, a substituted or unsubstituted alkynyl group, a substituted or unsubstituted aryl group or a substituted or unsubstituted heterocyclic group, $W^1$ is an oxygen atom or a sulfur atom, and n is 1 or 2); (b) a benzoylurea compound; (c) a pyrethroid compound and (d) a hydrazone compound of the formula (II) or its salt:

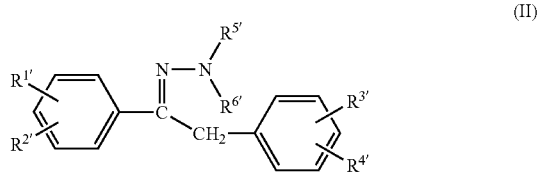

wherein each of $R^{1'}$, $R^{2'}$ and $R^{4'}$, which are independent of one another, is a hydrogen atom, a halogen atom, an alkyl group which may be substituted by halogen, or an alkoxy group which may be substituted by halogen, $R^{3'}$ is a halogen atom, an alkyl group which may be substituted by halogen, or an alkoxy group which may be substituted by halogen, $R^{5'}$ is a hydrogen atom, or an alkyl group, $R^{6'}$ is $X^{7'}$CO— (wherein $X^{7'}$ is a hydrogen atom, or an alkyl group), or $X^{8'}$OCO— (wherein $X^{8'}$ is an alkyl group), or $R^{5'}$ and $R^{6'}$ together form =$CR^{7'}R^{8'}$ (wherein $R^{7'}$ is a hydrogen atom, or an alkyl group, and $R^{8'}$ is an amino group which may be substituted by alkyl, or an alkoxy group), and a composition for controlling a house insect pest, which comprises, as an active ingredient, a hydrazone compound of the formula (II) or its salt.

Further, the present invention provides a method for controlling a house insect pest, which comprises applying such a composition to its habitat.

In the above formula (I), Y includes a haloalkyl group such as $CF_3$, $CHF_2$, $CH_2F$, $CF_2Cl$, $CFCl_2$, $CCl_3$, $CH_2CF_3$, $CF_2CF_3$, $CHBr_2$, $CH_2Br$ or the like. Among them, a haloalkyl group having a carbon number of from 1 to 2 and a halogen atom of from 1 to 5 is preferable, and a trifluoromethyl group is particularly preferable.

In the formula (I), examples of a secondary substituent of a substituted or unsubstituted alkyl group defined as $R^1$, $R^2$, $R^3$, $R^4$, $R^7$, $R^8$, $R^9$, $R^{10}$, $R^{11}$, $R^{12}$ or $R^{13}$ a substituted or unsubstituted alkenyl group defined as $R^1$, $R^2$, $R^3$, $R^4$, $R^8$, $R^9$, $R^{10}$, $R^{11}$, $R^{12}$ or $R^{13}$; a substituted or unsubstituted alkynyl group defined as $R^1$, $R^2$, $R^3$, $R^4$, $R^8$, $R^9$, $R^{12}$ or $R^{13}$; and a substituted or unsubstituted cycloalkyl group defined as $R^1$, $R^2$, $R^3$ or $R^4$ included in the group expressed by Q:

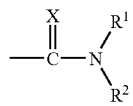

(hereinafter referred to as "$Q^1$ group"), include a halogen atom; an alkoxy group; an alkylthio group; a trialkylsilyl group; a phenyl group; a phenyl group substituted with a halogen, alkyl, alkoxy, nitro or haloalkyl group; a phenyl group substituted with a phenoxy group which may be substituted with an alkoxy or alkylthio group; a phenoxy group; a phenylthio group; an amino group; an amino group substituted with one or two alkyl group; a $C_{2-6}$ cyclic amino group; a morpholino group; a morpholino group substituted with an alkyl group; a 1-piperazinyl group; a 1-piperazinyl group substituted with an alkyl, phenyl, pyridyl or trifluoromethylpyridyl group; a heterocyclic group which may be substituted with a halogen, alkyl, alkoxy, haloalkoxy, alkylthio, phenyl (which may be further substituted with a halogen, alkyl, alkoxy, nitro, haloalkyl or phenoxy group), phenoxy, phenylthio, cycloalkyl or cycloalkoxy group; a hydroxy group; a cyano group; a cycloalkyl group; an imino group; a —$C(W^2)R^{14}$ group ($W^2$ is an oxygen atom or a sulfur atom, $R^{14}$ is a hydrogen atom; an amino group; an amino group substituted with one or two alkyl group; an alkyl group; an alkoxy group; an alkylthio group or an aryl group); a —$OC(W^2)R^{15}$ group ($R^{15}$ is an aryl group substituted with an alkyl or haloalkyl group); or an alkylsulfonyl group. Also, when the above substituent is an imino group, it may form an amidino group or an imidate group, together with an amino group or an alkoxy group.

Also, other examples of a substituent of a substituted or unsubstituted alkyl group defined as $R^1$ or $R^2$ included in the $Q^1$ group in the formula (I), include a 4-haloalkyl-3-pyridinecarboxyamide group, a N-methyl-4-haloalkyl-3-pyridinecarboxyamide group, a 4-haloalkyl-3-pyridinecarboxyamide-N-alkylenoxy group, and the like.

Thus, the above compound is a dimer of a compound of the formula (I) connected by way of an alkylene chain. In the same manner as above, the active ingredient of the composition for controlling a house insect pest of the present invention includes a trimer.

Examples of a secondary substituent of a substituted or unsubstituted aryl group defined as $R^1$, $R^2$, $R^3$, $R^4$, $R^8$, $R^9$, $R^{12}$ or $R^{13}$ included in the Q1 group in the formula (I), include a halogen atom; an alkyl group; a haloalkyl group; an alkoxy group; a haloalkoxy group; an alkylthio group; a cycloalkyl group; a cycloalkoxy group; an alkoxycarbonyl group; an alkylcarbonyl group; an alkylcarbonyloxy group; an aryl group; an aryloxy group; an arylthio group; an amino group; an amino group substituted with 1 or 2 alkyl group; a cyano group; a nitro group; a hydroxy group; and the like.

Examples of a secondary substituent of a substituted or unsubstituted heterocyclic group defined as $R^4$, $R^8$, $R^9$, $R^{10}$, $R^{11}$, $R^{12}$ or $R^{13}$ included in the $Q^1$ group in the formula (I), include a halogen atom; an alkyl group; an alkoxy group; a haloalkoxy group; an alkylthio group; a phenyl group which may be substituted with a halogen, alkyl, alkoxy, nitro, haloalkyl or phenoxy group; a phenoxy group; a phenylthio group; a cycloalkyl group; a cycloalkoxy group; and the like.

Examples of an alkyl moiety or an alkyl group included in the $Q^1$ group in the formula (I) include a group having a carbon number of from 1 to 6 such as a methyl group, an ethyl group, a propyl group, a butyl group, a pentyl group, a hexyl group and the like, and a group having a carbon number of at least 3 may include a linear or branched chain structure isomer. Examples of an alkenyl group included in the $Q^1$ group in the formula (I) include a group having a carbon number of from 2 to 6 such as an ethenyl group, a propenyl group, a butenyl group, a pentenyl group, a hexenyl group and the like, and a group having a carbon number of at least 3 may include a linear or branched chain structure isomer. Examples of an alkynyl group included in the $Q^1$ group in the formula (I) include a group having a carbon number of from 2 to 6 such as an ethynyl group, a propynyl group, a butynyl group, a pentynyl group, a hexynyl group, and a group having a carbon number of at least 4 may include a linear of branched chain structure isomer. Examples of a cycloalkyl group included in the $Q^1$ group in the formula (I) include a group having a carbon number of from 3 to 8 such as a cyclopropyl group, a cyclobutyl group, a cyclopentyl group or a cyclohexyl group.

Examples of a $C_4$-$C_5$ 5-membered or 6-membered heterocyclic group which may contain a nitrogen atom or an oxygen atom, formed from $R^1$ and $R^2$ together with an adjacent nitrogen atom, included in the $Q^1$ group in the formula (I), include a morpholino group, a pyrrolidino group, a piperidino group, a 1-imidazolidinyl group, a 2-cyanoimino-3-methyl-1-imidazolidinyl group, a 1-piperazinyl group or a 4-methyl-1-piperazinyl group.

Examples of an aryl group included in the $Q^1$ group in the formula (I) include a phenyl group, a thienyl group, a furanyl group, a pyridyl group, a naphthyl group, a benzothienyl group, a benzofuranyl group, a quinolinyl group and the like.

Examples of a heterocyclic moiety of a substituted or unsubstituted heterocyclic group included in the $Q^1$ group in the formula (I) include a 5 to 7-membered monocyclic or phenyl-condensed cyclic group containing 1 to 3 hetero atoms selected from a nitrogen atom, an oxygen atom and a sulfur atom, such as a pyridyl group, a thienyl group, a furyl group, a pirazinyl group, a pyrimidinyl group, a tetrahydrofuranyl group, a thiazolyl group, an isooxazolyl group, a quinolyl group, a pyrazolyl group, an oxazolyl group, an oxadiazolyl group, a thiadiazolyl group, a triazolyl group and the like.

Examples of a heterocyclic moiety of a substituted or unsubstituted heterocyclic group represented by Q in the formula (I) include preferably a 5 to 7-membered monocyclic group containing 2 to 3 hetero atoms selected from a nitrogen atom, an oxygen atom and a sulfur atom, such as a 5-membered monocyclic group including a pyrazolyl group, an oxazolyl group, a thiazolyl group, an oxydiazolyl group, a thiadiazolyl group, a triazolyl group and the like; and a 6-membered monocyclic group such as:

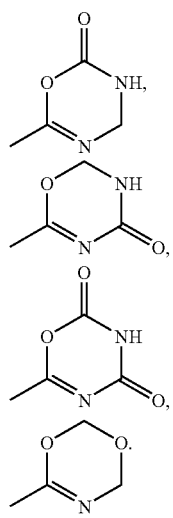

Examples of a secondary substituent of a substituted or unsubstituted heterocyclic group expressed by Q in the formula (I) include a halogen atom, a nitro group, a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted cycloalkyl group, a hydroxyl group, a substituted or unsubstituted alkoxy group, a substituted or unsubstituted alkenyloxy group, a substituted or unsubstituted alkynyloxy group, a substituted or unsubstituted aryloxy group, a substituted or unsubstituted heterocyclicoxy group, a substituted or unsubstituted cycloalkoxy group, a mercapto group, a substituted or unsubstituted alkylthio group, a substituted or unsubstituted alkenylthio group, a substituted or unsubstituted alkynylthio group, a substituted or unsubstituted arylthio group, a substituted or unsubstituted heterocyclicthio group, a substituted or unsubstituted cycloalkylthio group, a substituted or unsubstituted carbonyl group, a substituted or unsubstituted alkoxycarbonyl group, a substituted or unsubstituted arylcarbonyl group, a substituted or unsubstituted carbonyloxy group, a formyl group, a substituted or unsubstituted ester group, a substituted or unsubstituted acyl group, a substituted or unsubstituted sulfonyl group, a substituted or unsubstituted sulfyl group, a substituted or unsubstituted sulfonyloxy group, a substituted or unsubstituted alkylsulfyl group, a substituted or unsubstituted sulfonylalkyl group, a substituted or unsubstituted amino group, a substituted or unsubstituted isocyanate group, a substituted or unsubstituted arylalkyl group, a substituted or unsubstituted heterocyclic alkyl group, and the like.

Among these secondary substituents, some substituents may further be substituted with a tertiary substituent such as a halogen atom; a cyano group; an alkyl group which may be substituted with halogen, haloalkyl, cyano, alkoxy or aryl; an alkoxy group which may be substituted with halogen or aryl; a hydroxyl group; an amino group which may be substituted with alkylsulfonyl, arylalkyl, heterocyclic alkyl, alkyl, aryl, alkylaryl, alkylhydroxy, cyanoalkyl, alkynyl, alkenyl or cycloalkyl; a carbonyl group which may be substituted with alkoxy, alkylamino or alkyl; an alkylthio group; an aryloxy group; an arylthio group; an aryl group which may be substituted with halogen, haloalkoxy, alkyl or aryl; a nitro group; an arylcarbonyloxy group which may be substituted with halogen or nitro; a cycloalkyl group; an alkylsulfonyloxy group; an alkylcarbonyloxy group; an isocyanate group which may be substituted with alkyl, haloalkyl, alkenyl, alkynyl, heterocyclic alkyl, aryloxy, aryloxyalkyl, alkoxy, alkoxycarbonylalkyl, hydroxyalkyl, cyanoalkyl, alkoxyalkyl, alkenyl, arylalkoxy or alkoxycarbonylalkyl; an arylalkylisocyanate group which may be substituted with arylalkyl, halogen, alkyl or alkoxy; a cycloalkylcarbonyloxy group; a cycloalkylisocyanate group which may be substituted with haloalkyl; an alkynylalkylisocyanate group; an arylisocyanate group which may be substituted with alkyl, alkoxy, alkylthio, halogen, hydroxyl group, haloalkoxy, nitro, halogen-substituted aryloxy or aryloxy; a heterocyclic group which may be substituted with alkyl, alkoxy, aryl or ester; an alkoxyisocyano group; and the like.

Examples of an alkyl moiety or an alkyl group in a secondary substituent or a tertiary substituent of a substituted or unsubstituted heterocyclic group expressed by Q in the formula (I), include a group having a carbon number of from 1 to 6, such as a methyl group, an ethyl group, a propyl group, a butyl group, a pentyl group or a hexyl group, and a group having at least 3 carbon atoms may be a linear or branched chain structure isomer. Examples of an alkenyl group include a group having a carbon number of from 2 to 6, such as an ethenyl group, a propenyl group, a butenyl group, a pentenyl group or a hexenyl group, and a group having at least 3 carbon atoms may be a linear or branched chain structure isomer. Examples of an alkynyl group include a group having a carbon number of from 2 to 6, such as an ethynyl group, a propynyl group, a butynyl group, a pentynyl group or a hexynyl group, and a group having at least 3 carbon atoms may be a linear or branched chain structure isomer. Examples of a cycloalkyl group include a group having a carbon number of from 3 to 8, such as a cyclopropyl group, a cyclobutyl group, a cyclopentyl group or a cyclohexyl group. Examples of an aryl group include a phenyl group, a thienyl group, a furanyl group, a pyridyl group, a naphthyl group, a benzothienyl group, a benzofuranyl group or a quinolinyl group. Examples of a heterocyclic group include a 5-membered or 6-membered monocyclic or phenyl-condensed cyclic group having 1 to 3 hetero atoms selected from a nitrogen atom, an oxygen atom and a sulfur atom, such as a pyridyl group, a thienyl group, a furyl group, a pyrazinyl group, a thiazolyl group, an isooxazolyl group and a quinolyl group and the like.

A compound of the formula (I) may form a salt with an acidic material or a basic material, and examples of a salt with an acidic material include an inorganic acid salt such as a hydrochloride, a hydrobromide, a phosphate, a sulfate or a nitrate, and examples of a salt with a basic material include an inorganic or organic base salt such as a sodium salt, a potassium salt, a calcium salt, an ammonium salt or a dimethylamine salt.

A compound of the formula (I) or its salt can be produced in accordance with a method described in U.S. Pat. No. 5,360,806, WO98/57969, or the like.

Examples of an alkyl group or an alkyl moiety included in the formula (II) include a group having a carbon number of from 1 to 6 such as a methyl group, an ethyl group, a propyl group, a butyl group, a pentyl group or a hexyl group, examples of an alkenyl group or an alkenyl moiety include a group having a carbon number of from 2 to 6 such as a vinyl group, a propenyl group, a butenyl group, a pentenyl group or a hexenyl group, and examples of an alkynyl group or an alkynyl moiety include a group having a carbon number of from 2 to 6 such as an ethynyl group, a propynyl group, a butynyl group, a pentynyl group or a hexynyl group. Such respective groups and moieties include structural isomers of linear and branched aliphatic chains.

Examples of a halogen atom included in the formula (II) include a fluorine atom, a chlorine atom, a bromine atom or an iodine atom.

A compound of the formula (II) may form a salt with an acidic material or a basic material, and examples of a salt with an acidic material include an inorganic acid salt such as a hydrochloride or a sulfate, and examples of a salt with a basic material include an inorganic or organic base salt such as a sodium salt, a potassium salt, a calcium salt, an ammonium salt or a dimethylamine salt.

Further, the compounds of the formula (II) have geometrical isomers, i.e. E-form and Z-form, by virtue of the double bond of the hydrazones. The present invention includes such isomers and mixtures of such isomers.

In the present invention, the house insect pest is meant for an insect pest living in a house or around it. Specifically, it may, for example, be a termite, an ant or a cockroach. The composition of the present invention is useful as a composition for controlling the above-mentioned various house insect pests. It is particularly useful as a composition for controlling a termite, a composition for controlling an ant or a composition for controlling a cockroach. It is most useful as a composition for controlling a termite.

Examples of the termite which can be controlled by using the composition of the present invention and the active ingredients, include Mastotermitidae, Termopsidae (*Zootermopsis, Archotermopsis, Hodotermopsis, Porotermes* and *Stolotermes*), Kalotermitidae (*Kalotermes, Neotermes, Cryptotermes, Incisitermes* and *Glyptotermes*), Hodotermitidae (*Hodotermes, Microhodotermes* and *Anacanthotermes*), Rhinotermitidae (*Reticulitermes, Heterotermes, Coptotermes* and *Schedolinotermes*), Serritermitidae and Termitidae (*Amitermes, Drepanotermes, Hopitalitermes, Trinervitermes, Macrotermes, Odontotermes, Microtermes, Nasutitermes, Pericapritermes* and *Anoplotermes*).

Particularly, types of the termite to be controlled in Japan, include, for example, *Reticulitermes speratus, Coptotermes formosanus, Incisitermes minor, Cryptotermes domesticus, Odontotermes formosanus, Neotermeskoshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapriterme nitobei* and *Sinocapritermes mushae*.

Examples of the ant which can be controlled by using the composition of the present invention and the active ingredients, include Brachyponera chinensis, *Pheidole nodus, Crematogaster osakensis, Crematogaster laboriosa, Formica japonica, Lasius juponicus, Polyergus samurai, Monomorium intrudens, Monomorium pharaonis, Tetramorium caespitum* and fire ant.

Examples of the cockroach which can be controlled by using the composition of the present invention and the active ingredients, include *Blattella germanica, Blattella nipponica, Periplaneta fuliginosa, Periplaneta americana, Periplaneta australasiae, Periplaneta brunnea, Blatta orientalis, Periplaneta japonica, Periplaneta japanna, Neostylopyga rhombifolia, Hebardina yayeyamana, Rhabdoblatta formosana, Trichoblatta pygmaea* and *Panesthia angustipennis spadica*.

The blend ratio for a two component mixture in the present invention, i.e. the blend ratio of active ingredients (a) and (b), (a) and (c), (a) and (d), (b) and (c), (b) and (d), or (c) and (d), is from 1:1,000 to 1,000:1, preferably from 1:1,000 to 100:1, more preferably from 1:1,000 to 50:1. The blend ratio for a three component mixture in the present invention, i.e. the blend ratio of active ingredients (a), (b) and (c); (a), (b) and (d); (a), (c) and (d); or (b), (c) and (d), is such that the blend ratio of each of the above-mentioned two component mixtures, and another component, is from 1:1,000 to 1,000:1. The blend ratio for a four component mixture in the present invention, i.e. the blend ratio of active ingredients (a), (b), (c) and (d) is such that the blend ratio of each of the above-mentioned three component mixtures, and another component, is from 1:1,000 to 1,000:1. Further, the blend ratio of active ingredients (a) and (b), (b) and (d), or (a) and (d) in the present invention, is most preferably from 1:50 to 1:5, from 1:1,000 to 1:10, or from 10:1 to 50:1, respectively.

The composition of the present invention may be formulated together with adjuvants into various forms such as emulsifiable concentrates, suspension concentrates, wettable powders, water soluble powders, soluble concentrates, floable, water dispersible granules, granules, dusts, aerosols, pastes, poison bait chemicals, gel, formulated sheet, ultra-low volume concentrates and the like, in the same manner as in a case of conventional agricultural chemicals, and may be used as a composition for controlling house insect pests. Such formulations are usually composed of 0.001 to 99 parts by weight, preferably 0.01 to 95 parts by weight, more preferably 0.01 to 80 parts by weight of an active ingredient and 1 to 99.999 parts by weight, preferably 5 to 99.99 parts by weight, more preferably 20 to 99.99 parts by weight of adjuvants. When such formulations are to be actually used, they may be used as they are or after being diluted with suitable diluents such as water to a predetermined concentration.

As the adjuvants, there may be mentioned carriers, emulsifiers, suspending agents, dispersants, extenders, penetrating agents, antifoaming agents, wetting agents, thickeners, preservatives or stabilizers. They may be added as the case requires. The carriers may be classified into solid carriers and liquid carriers. As the solid carriers, there may be mentioned powders of animal and plant origin, such as cellulose (including cellulose derivative), starch, activated carbon, soybean flour, wheat flour, wood powder, fish powder or powdered milk; or mineral powders such as titanium dioxide, talc, kaolin, bentonite, calcium carbonate, zeolite, diatomaceous earth, white carbon, clay or alumina, and the like. As the liquid carriers, there may be mentioned water; alcohols such as isopropyl alcohol or ethylene glycol; ketones such as cyclohexanone or methyl ethyl ketone; ethers such as dioxane or tetrahydrofuran; aliphatic hydrocarbons such as kerosine, light oil or the like; aromatic hydrocarbons such as xylene, trimethylbenzene, tetramethylbenzene, methylnaphthalene or solvent naphtha; halogenated hydrocarbons such as chlorobenzene; acid amides such as dimethylformamide; esters such as glycerine ester of a fatty acid; nitrites such as acetonitrile; sulfur-containing compounds such as dimethyl sulfoxide; and the like.

The composition of the present invention may be applied to the habitat of house insect pests. The habitat of house insect pests, may, for example, be a trail for house insect pests, such as an ant trail, a wood or a soil. The composition of the present invention may be applied to the habitat of house insect pests as formulated into e.g. a poison bait chemical, a dust, a paste or a gel, so that it may be fed or contacted to the house insect pests, whereby the house insect pests can be controlled. Especially, to control termites or ants, it is advisable to adopt ① a method wherein the above-mentioned poison bait chemical is set in a baiting system, or ② a method wherein the above-mentioned dust, paste, gel or the like is applied to an ant trail or is directly coated to the damaged portion.

In an application of the composition of the present invention to an ant trail, it is advisable to destroy a part of the ant trail and apply the composition to the interior of the ant trail. Further, in a case where the composition of the present invention is to be applied to a wood or to the habitat of house insect pests, spray treatment or coating treatment may be employed. When the composition of the present invention formulated into a dust, a paste, a gel or the like, is to be coated to the wood, perforations may be formed for injection treatment through the perforations, as the case requires.

By applying the composition of the present invention as a poison bait chemical to an ant trail or around the ant trail, it is possible to exterminate nests of termites or ants. For example, in a case where an ant trail is present under floor or the like, a part of the ant trail is broken and the composition of the present invention is applied or injected. Otherwise, a poison bait chemical is set around a building by utilizing the nature of termites or ants always looking for a bait, to exterminate them by letting them take in the composition of the present invention. If the poison bait chemical of the composition of the present invention is applied or set, termite workers or worker ants would eat the bait, continue to invite other termites or ants to the bait to let them continuously die, or termite workers or worker ants take the bait back to their nests and give the bait to termite soldiers or soldier ants, larvae, termite queen or queen ant, so that the poison bait chemical containing the composition of the present invention will be distributed in the nest and thereby to destroy the nest. Further, the poison bait chemical may be set in a baiting system such as a bait station, which may be set at or around an ant trail or around a building.

The composition of the present invention may be used for soil treatment in such a manner that a layer of the chemical is formed at the soil surface. More specifically, for example, when a liquid formulation is applied to e.g. under floor soil of a wood building where human can enter, the application may be made by means of a power sprayer, and it is particularly preferred to primarily treat the base portion of a building where an ant trail is likely to be formed. Further, in order to treat under floor soil or the like where human can not enter, such as under floor for bathroom or the front door, a method will be employed wherein a hole is drilled, and the chemical will be injected to soil therethrough. Otherwise, the composition of the present invention may be applied to soil in the form of a granule or a dust.

The composition of the present invention may be formulated into an aerosol containing the above dust. The aerosol usually comprises the above dust and a propellant, and, if necessary, a solvent. Such an aerosol usually contains the dust in an amount of from 0.1 to 10 wt % and the propellant in an amount of from 20 to 90 wt %. Further, the solvent may, for example, be an ester such as isopropyl myristate, isopropyl palmitate, isopropyl decanoate or isopropyl laurate; or an alcohol such as ethanol or isopropyl alcohol.

When the composition of the present invention takes a form of a formulated sheet, it may contain the compound of the active ingredients usually in a concentration of from 0.01 to 20 wt % in the formulated sheet. The formulated sheet may be produced in accordance with a conventional method by having the compounds of the active ingredients supported on a carrier of a sheet shape such as a cellulose sheet. For example, a solution or dispersion containing the compounds of the active ingredients may be coated on a cellulose paper, followed by drying to obtain a formulated sheet. Such a solution or dispersion may be obtained by dissolving or dispersing the compounds of the active ingredients in a suitable solvent, but, if necessary, it can be diluted with a water containing a surfactant or a dispersant.

When the composition of the present invention is to be used for controlling a house insect pest, the dose of the active ingredients may vary depending upon the application method of the composition of the present invention, the formulation and various other conditions, but is usually from 0.1 to 100 g/m$^2$, preferably from 0.5 to 20 g/m$^2$, in the case of soil treatment, and from 0.01 to 50 g/m$^2$, preferably from 0.1 to 5 g/m$^2$, in the case of wood treatment. Further, when it is applied as a poison bait chemical, the amount of the active ingredients is at a level of from 0.01 to 10 g per application site.

The composition of the present invention may contain in addition to the compounds of the active ingredients, fungicides of e.g. organosulfur compounds, organophosphorus compounds, organoarsenic compounds or organochlorine compounds; insecticides of e.g. organophosphorus compounds, organochlorine compounds, carbamates or chloronicotinyls, or various anti-biotics or one or more other agents for controlling house insect pests. Particularly, the composition of the present invention may contain insecticides, such as chitin synthesis inhibitors of e.g. organophosphorus compounds, carbamates or chloronicotinyls, or insect growth regulators having sclerotization activities or juvenile hormone mimic activities, or one or more termite-controlling active components, ant-controlling active components or cockroach-controlling active components. Further, an organophosphorus insecticide such as Phoxim, Chlorpyrifos, Pyridaphenthion, Fenitrothion or Propetamphos; a carbamate insecticide such as Fenobucarb or Propoxur; a chloronicotinyl insecticide such as Imidacloprid; or an insecticide such as Sulfuramid or Hydramethylnon, may be particularly suitably incorporated to the composition of the present invention.

The composition of the present invention is excellent in the activities for controlling house insect pests and soil stability, has preventive activities against house insect pests and has lasting activities against house insect pests. Further, such a composition makes it possible to reduce the dose of the chemical and thus makes it possible to reduce health problems or problems of environmental pollution.

BEST MODE FOR CARRYING OUT THE INVENTION

Now, some of preferred embodiments of the compositions for controlling house insect pests according to the present invention, will be exemplified. However, the present invention is by no means restricted to such preferred embodiments.

Preferred compounds as the active ingredient (a) will be given below. However, compounds which can be used as the active ingredient (a), are not limited thereto. Further, the active ingredient (a) is a compound which is preferred also in a case where it is used alone as an active ingredient in a composition for controlling a house insect pest.

(a-1) A pyridine compound of the formula (I) or its salt:

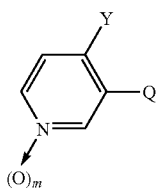

(I)

wherein Y, m and Q are as defined above.

(a-2) A compound or its salt of the above (a-1) wherein Q is:

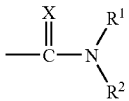

wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, a —$C(W^1)R^3$ group, a —$S(O)_nR^5$ group, a —$NHR^6$ group,

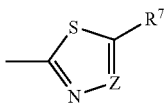

or a —$C(R^8)$=NO—$R^9$ group, or $R^1$ and $R^2$ may form a =$C(R^{10})R^{11}$ group or may form a $C_4$-$C_5$ 5-membered or 6-membered heterocyclic group which may contain a nitrogen atom or an oxygen atom, together with an adjacent nitrogen atom, and $R^3$, $R^5$, $R^6$, Z, $R^7$, $R^8$, $R^9$, $R^{10}$, $R^{11}$, $W^1$ and n are as defined above.

(a-3) A compound or its salt of the above (a-1), wherein Q is:

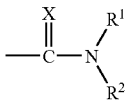

(wherein X is an oxygen atom or a sulfur atom, $R^1$ and $R^2$ are respectively independently a hydrogen atom, a substituted or unsubstituted alkyl group, a substituted or unsubstituted alkenyl group, a substituted or unsubstituted alkynyl group, a substituted or unsubstituted cycloalkyl group, a —$C(W^1)R^3$ group, a —$S(O)_nR^5$ group or a —$NHR^6$ group, or $R^1$ and $R^2$ may form a =$C(R^{10})R^{11}$ group or may form a $C_4$-$C_5$ 5-membered or 6-membered heterocyclic group which may contain a nitrogen atom or an oxygen atom, together with an adjacent nitrogen atom, and $R^3$, $R^5$, $R^6$, $W^1$ and n are as defined above, and $R^{10}$ and $R^{11}$ are respectively independently an alkoxy group or an alkylthio group.

(a-4) A compound or its salt of the above (a-1), wherein Q is:

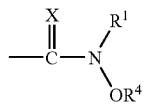

wherein X is an oxygen atom or a sulfur atom, $R^1$ is a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted aryl group or a —$C(W^1)R^3$ group, and $R^3$, $R^4$ and $W^1$ are as defined above.

(a-5) A compound or its salt of the above (a-2) or (a-3), wherein X is an oxygen atom.

(a-6) A compound or its salt of the above (a-3), wherein $R^1$ and $R^2$ are respectively independently a hydrogen atom, a substituted or unsubstituted alkyl group or a —$C(W^1)R^3$ group, or $R^1$ and $R^2$ may form a =$C(R^{10})R^{11}$ group, $W^1$ is an oxygen atom or a sulfur atom, $R^3$ is a substituted or unsubstituted alkyl group, a substituted or unsubstituted aryl group or an alkoxy group, and $R^{10}$ and $R^{11}$ are respectively independently an alkoxy group or an alkylthio group.

(a-7) A compound or its salt of the above (a-2), wherein $R^1$ is a hydrogen atom, $R^2$ is a —$C(R^8)$=NO—$R^9$ group, and $R^8$ and $R^9$ are as defined above.

(a-8) A compound or its salt of the above (a-2), wherein $R^1$ and $R^2$ form a =$C(R^{10})$—$N(R^{12})R^{13}$ group, and $R^{10}$ is a hydrogen atom, a substituted or unsubstituted alkyl group, a substituted or unsubstituted alkenyl group or a substituted or unsubstituted heterocyclic group, and $R^{12}$ and $R^{13}$ are as defined above.

(a-9) A compound or its salt of the above (a-2), wherein $R^1$ is a hydrogen atom, and $R^2$ is

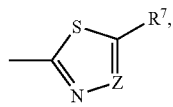

(wherein Z and R7 are as defined above).

(a-10) A compound or its salt of the above (a-3), wherein is an oxygen atom, $R^1$ and $R^2$ are respectively independently a hydrogen atom, an alkyl group, an alkoxyalkyl group, an alkylaminoalkyl group, a $C_{2-6}$ cyclic aminoalkyl group, a hydroxyalkyl group, a cyanoalkyl group, a thiocarbamoylalkyl group, an alkylcarbonyloxyalkyl group, an alkylcarbonyl group, an arylcarbonyl group, a trifluoromethyl-substituted arylcarbonyl group, an alkoxythiocarbonyl group or an alkoxycarbonyl group, or $R^1$ and $R^2$ may form a =$C(R^{10})R^{11}$ group, and $R^{10}$ and $R^{11}$ are respectively an alkoxy group and an alkylthio group.

(a-11) A compound or its salt of the above (a-1), wherein the compound of the formula (I) is at least one member selected from the group consisting of N-cyanomethyl-4-trifluoromethyl-3-pyridinecarboxyamide (Compound No. I-1), N-ethyl-4-trifluoromethyl-3-pyridinecarboxyamide (Compound No. I-2), 4-trifluoromethyl-3-pyridinecarboxyamide (Compound No. I-3), N-thiocarbamoylmethyl-4-trifluoromethyl-3-pyridinecarboxyamide (Compound No. I-4), N-ethoxymethyl-4-trifluoromethyl-3-pyridinecarboxyamide (Compound No. I-5), N-isopropylaminomethyl-4-trifluoromethyl-3-pyridinecarboxyamide (Compound No. I-6), N-cyanomethyl-N,N-bis(4-trifluoromethylnicotinoyl)amine (Compound No. I-7), N-acetyl-N-cyanomethyl-4-trifluoromethyl-3-pyridinecarboxyamide (Compound No. I-8), N-cyanomethyl-N-methyl-4-trifluoromethylpyridine-3-carboxyamide (Compound No. I-9), O-methyl N-(4-trifluoromethylnicotinoyl)thiocarbamate (Compound No. I-10), N-methyl-4-trifluoromethylpyridine-3-carboxyamide (Compound No. I-11), N-(N',N'-diemthylaminomethyl)-4-trifluoromethylpyridine-3-carboxyamide (Compound No. I-12), N-(1-piperidylmethyl)-4-trifluoromethylpyridine-3-carboxyamide (Compound No. I-13), N-cyanomethyl N-(4-trifluoromethylnicotinoyl)aminomethylpivalate (Compound No. I-14), O,S-dimethyl N-(4-trifluoromethylnicotinoyl)iminoformate (Compound No. I-15), N-hydroxymethyl-4-trifluoromethyl-3-pyridinecarboxyamide (Compound No. I-16), N-acetyl-4-trifluoromethyl-3-pyridinecarboxyamide (Compound No. I-17) and methyl N-(4-trifluoromethylnicotinoyl)carbamate (Compound No. I-18) or their 1-oxides.

(a-12) A compound or its salt of the above (a-1), wherein a compound of the formula (I) is N-cyanomethyl-4-trifluoromethyl-3-pyridinecarboxyamide.

(a-13) A compound or its salt of the above (a-1), wherein Q is a substituted or unsubstituted heterocyclic group.

(a-14) A compound or its salt of the above (a-13), wherein the heterocyclic group moiety is a 5 to 7-membered monocyclic group having 2 to 3 hetero atoms selected from the group consisting of a nitrogen atom, an oxygen atom and a sulfur atom.

(a-15) A compound or its salt of the above (a-13), wherein the heterocyclic group moiety is a 5-membered monocyclic group containing 2 to 3 hetero atoms selected from the group consisting of a nitrogen atom, an oxygen atom and a sulfur atom.

(a-16) A compound or its salt of the above (a-15), wherein the 5-membered monocyclic group is a pyrazolyl group, an oxazolyl group, a thiazolyl group, an oxydiazolyl group, a thiadiazolyl group or a triazolyl group.

(a-17) A compound or its salt of the above (a-13), wherein the heterocyclic group moiety is a 6-membered monocyclic group containing 2 to 3 hetero atoms selected from the group consisting of a nitrogen atom, an oxygen atom and a sulfur atom.

(a-18) A compound or its salt of the above (a-17), wherein the 6-membered monocyclic group is:

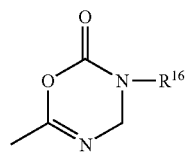

(wherein $R^{16}$ is an alkyl group).

(a-19) A compound or its salt of the above (a-18), wherein $R^{16}$ is a methyl group or an isopropyl group.

Benzoylurea compounds preferred as the active ingredient (b) will be given below. However, the active ingredient (b) is not limited to such specific examples.
(b-1) Diflubenzuron
(b-2) Chlorfluazuron
(b-3) Teflubenzuron
(b-4) Flufenoxuron
(b-5) Triflumuron
(b-6) Hexaflumuron
(b-7) Lufenuron
(b-8) Novaluron
(b-9) Noviflumuron As the benzoylurea compound of the active ingredient (b), it is preferred to employ at least one compound selected from the group consisting of Diflubenzuron, Chlorfluazuron, Hexaflumuron and Flufenoxuron, and it is further preferred to employ Chlorfluazuron and/or Hexaflumuron.

Now, pyrethroid compounds preferred as the active ingredient (c) will be given below. However, the active ingredient (c) is not limited thereto. The pyrethroid compounds have various optical isomers, and in the present invention, active optional isomers and their mixture may be used.
(c-1) Fenvalerate
(c-2) Permethrin
(c-3) Cypermethrin
(c-4) Deltamethrin
(c-5) Cyhalothrin
(c-6) Tefluthrin
(c-7) Ethofenprox
(c-8) Cyfluthrin
(c-9) Fenpropathrin
(c-10) Flucythrinate
(c-11) Fluvalinate
(c-12) Cycloprothrin
(c-13) Lambda-Cyhalothrin
(c-14) Pyrethrins
(c-15) Esfenvalerate
(c-16) Tetramethrin
(c-17) Resmethrin
(c-18) Protrifenbute
(c-19) Bifenthrin
(c-20) Acrinathrin
(c-21) S-cyano(3-phenoxyphenyl)methyl(±)cis/trans3-(2,2-dichloroethenyl)-2,2dimethylcyclopropane carboxylate As the pyrethroid compound of the active ingredient (c), it is more preferred to employ at least one compound selected from the group consisting of Flucythrinate, Cycloprothrin, Bifenthrin and Acrinathrin, and it is further preferred to employ Bifenthrin.

As the hydrazone compound or its salt, as the active ingredient (d), it is preferred to employ at least one compound or its salt selected from the group consisting of [4'-chloro-2-(4-trifluoromethylphenyl)acetophenone]N'-[1-(dimethylamino)ethylidene]hydrazone (Compound No. II-1), [4'-fluoro-2-(4-trifluoromethylphenyl)acetophenone]N'-[1-(dimethylamino)ethylidene]hydrazone (Compound No. II-2), ethyl 3-[1-(4-chlorophenyl-2-(4-trifluoromethylphenyl)ethylidene]carbazate (Compound No. II-3), [4'-chloro-2-(4-tert-butylphenyl)acetophenone]N'-[1-(dimethylamino)ethylidene]hydrazone (Compound No. II-4), [4'-fluoro-2-(4-tert-butylphenyl)acetophenone]N'-[1-dimethylamino)ethylidene]hydrazone (Compound No. II-5), [4'-methyl-2-(4-tert-butylphenyl)acetophenone]N'-[1-(dimethylamino)ethylidene]hydrazone (Compound No. II-6) and [4'-chloro-2-(4-trifluoromethylphenyl)acetophenone]N'-[1- aminoethylidene]hydrazone (Compound No. II-7). Further, the active ingredient (d) is a compound which is also preferred in a case where it is used alone as an active ingredient in a composition for controlling a house insect pest.

The hydrazone compound of the formula (II) or its salt, may be produced in accordance with the method disclosed in U.S. Pat. No. 5,288,727.

Among compositions for controlling house insect pests of the present invention, which contain the hydrazone compound of the formula (II) or its salt, preferred embodiments will be given below.

(1) A composition in the form of a poison bait chemical which contains the hydrazone compound of the formula (II) or its salt.
(2) The composition as defined in (1) wherein a bait log, fresh pulp or pulp is used as the base material for the poison bait chemical.
(3) The composition as defined in (1) wherein fresh pulp is used as the base material for the poison bait chemical.
(4) The composition as defined in (1) wherein a bait log is used as the base material for the poison bait chemical.
(5) The composition as defined in (1) wherein a bait log of conifer type is used as the base material for the poison bait chemical.
(6) The composition as defined in (5) wherein the bait log of conifer type is one obtained by boiling a conifer in hot water.
(7) The composition as defined in (5) or (6), wherein the bait log of conifer type is pine.
(8) The composition as defined in (7) wherein the pine is Japanese larch.
(9) A composition in the form of a gel which comprises the hydrazone compound of the formula (II) or its salt, and a water-absorptive polymer and which has a water-holding property.
(10) A composition in the form of a dust which comprises the hydrazone compound of the formula (II) or its salt, and a solid carrier.
(11) A composition in the form of a soil treating agent which contains the hydrazone compound of the formula (II) or its salt.

Among the above embodiments, the composition for controlling a house inset pest, which is in the form of a poison bait chemical, will be explained. A house insect pest will not die immediately after ingesting the poison bait chemical and will bring the poison bait chemical into the nest. The poison bait chemical brought into the nest will be ingested by or contacted to other house insect pests. Consequently, it is possible to kill all of the house insect pests which ingested or were in contact with the poison bait chemical. The poison bait chemical is characterized by having such an effect (an effect of spread).

A conventional quick acting agent of an organic phosphorus type, a pyrethroid type or the like, has a repellent nature and will not be ingested by a house insect pest. Even if it is ingested, the house insect pest ingested it, will die immediately, whereby no effect of spread can be expected. Accordingly, it is common to employ a slow acting conventional agent such as a benzoyl urea compound as the active ingredient for a poison bait chemical. However, if a slow acting active ingredient is employed, although the effect of spread can be obtained, it takes from 2 to 3 months to kill the house insect pests in the entire nest, whereby the damage during the period can not be prevented. Whereas, the hydrazone compound of the above formula (II) or its salt has no repellent nature against house insect pests, and further has an adequate effect of spread, since it acts slowly as compared with the quick acting conventional agent. Further, it is thereby possible to extinct the nest of house insect pests in a short period of time (within one month) as compared with the slow effect of a poison bait chemical employing a conventional slow-acting agent as an active ingredient, whereby the damage by the house insect pests can be suppressed to a minimum level. Thus, the above-mentioned embodiment (2) is characterized in that it is a poison bait chemical of new type, which was not available heretofore.

As the base material for a poison bait chemical, various types may be mentioned, but a bait log, fresh pulp or pulp is preferred. As the bait log to be used as the base material, various types may be mentioned, but a bait log of conifer type such as pine, cedar or Hinoki cypress, is preferred. Among them, it is particularly preferred to employ pine. Further, among pines, it is further preferred to employ Japanese larch. Such a conifer type bait log is preferably a dead tree or one obtained by sufficiently boiling it in hot water to decoct components and insect pests in the bait log. The fresh pulp or pulp to be used as the base material is used as a cellulose source which will be a bait for house insect pests, particularly termites. As such pulp, KIMUTAORU (tradename, manufactured by CRECIA Co.) or KITCHENTOWEL (tradename, manufactured by NEPIA Co.) may, for example, be mentioned. The weight ratio of the hydrazone compound or its salt to the base material, is usually from 1:10,000 to 1:4, preferably from 1:1,000 to 1:9.

Among the above embodiments, the composition for controlling a house insect pest, which is in the form of a gel, will be explained. The gel may be applied to an ant trail as an ant trail-treating agent or may be coated directly to a damaged portion such as a wood. Otherwise, it may be coated on a bait wood, fresh pulp or pulp to form a poison bait chemical, which will be used as set in a baiting system, and it is particularly effective to use it as coated on a wood damaged by termites. Further, it is most effective to apply it to perforated portions of the wood damaged by termites. The water absorptive polymer to be used for the gel, may be used as the base material or may be contained as an additive in the agent for controlling a house insect pest. Otherwise, it may be used as a carrier for the agent for controlling a house insect pest. The water absorptive polymer may also be one having been swelled by having another component taken into the interior. The water absorptive polymer to be used, is preferably one having a water absorptivity of at least 10 times, preferably at least 100 times, its own weight. One having such a high water absorptivity may, for example, be an isobutylene/maleic anhydride copolymer, a polyacrylate polymer, a starch/polyacrylate polymer, a polyvinyl acetate/polyacrylate polymer, a carboxymethylcellulose polymer or a polyvinyl alcohol polymer. In a case where a water absorptive polymer is used as the base material, its amount is preferably from 0.05 to 10 wt %, more preferably from 0.1 to 5%, in the total weight.

Among the above embodiments, the dust will be explained. The dust may be applied to an ant trail as an ant trail treating agent or used as a poison bait chemical as set in a baiting system. This dust is characterized in that the effect of spread is excellent as compared with conventional dusts. As the solid carrier to be used for this dust, the above-mentioned animal or plant powder, and/or a mineral powder is preferred, and among them, cellulose and/or titanium oxide is preferred. Here, the cellulose may be a commercially available cellulose such as crystalline cellulose; cellulose fiber such as pulp; a cellulose porous body such as cellulose beads; or a cellulose derivative such as carboxymethylcellulose or a cellulose ester. The weight ratio of the hydrazone compound or its salt to the solid carrier is usually from 1:10,000 to 1:4, preferably from 1:1,000 to 1:4.

Among the above embodiments, the soil treating agent will be explained. The soil treating agent is used in the form of an aqueous suspension, a granule, a dust or the like. For example, the aqueous suspension is applied to soil for use. When a soil treating agent containing the hydrazone compound or its salt at a concentration of from 10 to 50,000 ppm, preferably from 100 to 5,000 ppm, is applied to soil at a rate of from 0.1 to 100 g/m$^2$, preferably from 0.5 to 20 g/m$^2$, the after effect in soil becomes superior as compared with a conventional agent for controlling termites by soil treatment.

Preferred embodiments will be given below with respect to the method for controlling house insect pests by means of the composition for controlling a house insect pest of the present invention, but it should be understood that the present invention is by no means restricted thereto.

(1) A method for controlling a house insect pest, which comprises applying the composition of the present invention to the habitat of the house insect pest.

(2) The method of (1) wherein the composition of the present invention is fed or contacted to the house insect pest.

(3) The method of (1) or (2) wherein the habitat of the house insect pest is soil.

(4) The method of (1) or (2) wherein the habitat of the house insect pest is an ant trail.

(5) The method of (1) or (2) wherein the habitat of the house insect pest is a wood.

(6) The method of (1) wherein the composition for controlling a house insect pest is applied to an ant trail or coated directly to a damaged portion to control termites or ants.

(7) The method of (1) wherein the composition for controlling a house insect pest of the present invention in the form of a poison bait chemical, is set in a baiting system.

(8) The method of (7) wherein the baiting system is set at or around an ant trail or around a building.

(9) The method of (7) or (8), wherein the baiting system is a bait station.

(10) The method of (2) wherein the composition of the present invention in the form of a dust, paste or gel, is applied to an ant trail or coated directly to a damaged portion to control termites or ants.

(11) The method of (10) wherein the composition of the present invention in the form of a dust, paste or gel, is applied to an ant trail.

(12) The method of (10) wherein the composition of the present invention in the form of a dust, paste or gel is directly coated to a damaged portion.

Now, the present invention will be described in further detail with reference to Examples. However, it should be understood that the present invention is by no means restricted to such specific Examples.

TEST EXAMPLE 1

A filter paper having a diameter of 80 mm was placed in a plastic Petri dish, and 1 ml of a pesticide solution having a predetermined concentration was dropped thereon. After the treatment, the solvent was sufficiently evaporated, and then, 1 ml of distilled water was impregnated to the treated filter paper, whereupon 15 termite workers and one termite soldier (*Reticulitermes speratus*) were released. The plastic Petri dish was placed in a container having wet cotton laid over the bottom, and the container was maintained at 25° C. for 13 days, whereupon the number of dead termites in the Petri dish was examined, and the mortality was calculated by the following formula. The results are shown in Table 1.

Mortality (%)=(Number of dead termite workers/15 termite workers)×100

Further, by the Colby's formula, the theoretical value (%) of mortality can be calculated. In a case where the actual mortality (%) is higher than the theoretical value (%), it can be said that the composition of the present invention has a synergistic effect for controlling the house insect pest.

TABLE 1

| Compound | Chlorfluazuron Mortality [theoretical value] (%) | | | | |
| --- | --- | --- | --- | --- | --- |
| No. I-1 | 8000 ppm | 4000 ppm | 2000 ppm | 1000 ppm | 0 ppm |
| 200 ppm | — | 93 | 100 | 80 | 100 |
| 100 ppm | — | 80 [69] | 100 [55] | 93 [33] | 33 |
| 0 ppm | 60 | 53 | 33 | 0 | 0 |

TEST EXAMPLE 2

A filter paper having a diameter of 80 mm was placed in a plastic Petri dish, and 1 ml of a pesticide solution having a predetermined concentration, was dropped thereon. After the treatment, the solvent was sufficiently evaporated and then, 1 ml of distilled water was impregnated to the treated filter paper, whereupon 15 termite workers and one termite soldier (*Reticulitermes speratus*) were released. The plastic Petri dish was placed in a container having wet cotton laid over the bottom, and the container was maintained at 25° C. for 17 days. Then, the number of dead termites in the Petri dish was examined, and the mortality was calculated in the same manner as in Test Example 1. The results are shown in Table 2.

TABLE 2

| Compound | Hexaflumuron Mortality [theoretical value] (%) | | | | |
| --- | --- | --- | --- | --- | --- |
| No. I-1 | 8000 ppm | 4000 ppm | 2000 ppm | 1000 ppm | 0 ppm |
| 200 ppm | — | 100 | 100 | 100 | 100 |
| 100 ppm | — | 67 [52] | 100 [64] | 100 [64] | 40 |
| 0 ppm | 33 | 20 | 40 | 40 | 0 |

TEST EXAMPLE 3

A filter paper having a diameter of 80 mm was placed in a plastic Petri dish, and 1 ml of a pesticide solution having a predetermined concentration, was dropped thereon. After the treatment, the solvent was sufficiently evaporated, and then, 1 ml of distilled water was impregnated to the treated filter paper, whereupon 10 termite workers (*Reticulitermes speratus*) were released. The plastic Petri dish was placed in a container having wet cotton laid over the bottom, and the container was maintained at 25° C. for 37 days, whereupon the number of dead termites in the Petri dish was examined, and the mortality was calculated in the same manner as in Test Example 1. The results are shown in Table 3.

TABLE 3

| Compound | Chlorfluazuron Mortality [theoretical value] (%) | | | | |
|---|---|---|---|---|---|
| No. II-2 | 4000 ppm | 2000 ppm | 1000 ppm | 500 ppm | 0 ppm |
| 10 ppm | 90 [60] | 100 [60] | 80 [60] | 100 [44] | 20 |
| 5 ppm | 80 [60] | 80 [55] | 80 [55] | 60 [37] | 10 |
| 0 ppm | 50 | 50 | 50 | 30 | 10 |

TEST EXAMPLE 4

A filter paper having a diameter of 80 mm was placed in a plastic Petri dish, and 1 ml of a pesticide solution having a predetermined concentration, was dropped thereon. After the treatment, the solvent was sufficiently evaporated, and then, 1 ml of distilled water was impregnated to the treated filter paper, whereupon 10 termite workers (*Reticulitermes speratus*) were released. The plastic Petri dish was placed in a container having wet cotton laid over the bottom, and the container was maintained at 25° C. for 25 days, whereupon the number of dead termites in the Petri dish was examined, and the mortality was calculated in the same manner as in Test Example 1. The results are shown in Table 4.

TABLE 4

| | Compound No. I-1 Mortality [theoretical value] (%) | | |
|---|---|---|---|
| Compound No. II-2 | 100 ppm | 50 ppm | 0 ppm |
| 10 ppm | 100[19] | 100[10] | 10 |
| 5 ppm | 100[10] | 70[0] | 0 |
| 0 ppm | 10 | 0 | 10 |

TEST EXAMPLE 5

A filter paper having a diameter of 80 mm was placed in a cylindrical cup made of acrylic resin having a diameter of 80 mm and a height of 60 mm (i.e. a cup having a hole with a diameter of 10 mm formed in the bottom and having hard plaster (Dental Stone) set at the bottom in a thickness of 10 mm), and 1 ml of a solution containing a sample compound in a predetermined concentration, was dropped thereon. Then, nine termite workers and one termite soldier (*Coptotermes formosanus*) were released thereon. The cup was placed in a container having wet cotton laid over the bottom, and the container was maintained at room temperature of 25° C. for 7 days, whereupon the mortality of termites in the cup was examined. The results are shown in Table 5.

TABLE 5

| Sample compound | Concentration (ppm) | Mortality (%) |
|---|---|---|
| Compound No. I-1 | 1,000 | 100 |
| | 500 | 100 |
| Chlorpyrifos | 1,000 | 100 |
| | 500 | 100 |
| No treatment | — | 0 |

TEST EXAMPLE 6

A filter paper having a diameter of 80 mm was placed in a cylindrical cup made of acrylic resin having a diameter of 80 mm and a height of 60 mm (i.e. a cup having a hole with a diameter of 10 mm formed in the bottom and having hard plaster (Dental Stone) set at the bottom in a thickness of 10 mm), and 1 ml of a solution containing a sample compound in a predetermined concentration, was dropped thereon. Then, ten termite workers and one termite soldier (*Reticulitermes speratus*) were released thereon. The cup was placed in a container having wet cotton laid over the bottom, and the container was maintained at room temperature of 25° C. for 7 days, whereupon the mortality of termites in the cup was examined. The results are shown in Table 6.

TABLE 6

| Sample Compound | Concentration (ppm) | Mortality (%) |
|---|---|---|
| Compound No. I-1 | 1,000 | 100 |
| Chlorpyrifos | 1,000 | 100 |
| No treatment | — | 0 |

TEST EXAMPLE 7

A compound solution having a predetermined concentration was coated by a paint brush in an amount of 60 g/m² on a rectangular parallelepiped wood block of Japanese red pine of 20 mm (L)×10 mm (R)×10 mm (T). The treated wood block and a non-treated wood block were dried at a temperature of 60° C. for 48 hours, and their weights ($W_1$) were measured, and they were used as test specimens. Such a test specimen was put into a cylindrical cup made of acrylic resin (i.e. a cup having a hole with a diameter of 10 mm formed in the bottom and having hard plaster (Dental Stone) set at the bottom in a thickness of 10 mm), and 150 termite workers and 15 termite soldiers (*Reticulitermes speratus*) were released thereon. The cup was placed in a container having wet cotton laid over the bottom, and the container was maintained at room temperature of 25° C. for 21 days, whereupon the mortality of termites in the cup was examined. Further, the test specimen was taken out from the cup, and the deposited substance was removed from the surface of the test specimen. After drying at a temperature of 60° C. for 48 hours, it was weighed to obtain the weight ($W_2$), whereupon the mean weight loss of the wood block was calculated. The results are shown in Table 7.

Mean weight loss (%) of the wood block=$(W_1-W_2/W_1)\times 100$

TABLE 7

| Sample compound | Concentration (W/V %) | Mean weight loss (%) | Mortality of termite workers (%) |
|---|---|---|---|
| Compound No. I-1 | 1 | 0 | 100 |
| No treatment | — | 18 | 0 |

TEST EXAMPLE 8

A poison bait chemical comprising 1 g of powdered skim milk and 1% of a sample compound obtained by treating 1 ml of an acetone solution having a predetermined concentration and sufficiently evaporating acetone in a constant temperature chamber of 40° C. for 20 hours, was prepared. Then, this poison bait chemical was put into a cup together with a wet cotton, and 15 ants (*Lasius japonicus*) were released, and four days later, the mortality was examined. The results are shown in Table 8.

TABLE 8

| Sample compound | Bait concentration (%) | Mortality (%) |
|---|---|---|
| Compound No. I-1 | 1 | 86 |
| No treatment | — | 35 |

TEST EXAMPLE 9

A filter paper having a diameter of 80 mm was placed in a cylindrical cup made of acrylic resin having a diameter of 80 mm and a height of 60 mm (i.e. a cup having a hole with a diameter of 10 mm formed in the bottom and having hard plaster (Dental Stone) set at the bottom in a thickness of 10 mm), and 1 ml of a solution containing a sample compound in a predetermined concentration, was dropped thereon. Then, ten termite workers and one termite soldier (*Reticulitermes speratus*) were released thereon. The cup was placed in a container having wet cotton laid over the bottom, and the container was maintained at room temperature of 25° C., and 5 days later and 20 days later, the mortality of termites in the cup was examined. The results are shown in Table 9.

TABLE 9

| | | Mortality (%) | |
|---|---|---|---|
| Sample compound | Concentration (ppm) | 5 Days later | 20 Days later |
| Compound No. II-1 | 1000 | 0 | 100 |
| Compound No. II-2 | 1000 | 100 | 100 |
| Compound No. II-3 | 1000 | 0 | 100 |
| Compound No. II-6 | 1000 | 70 | 100 |
| Compound No. II-7 | 1000 | 100 | 100 |
| No treatment | — | 0 | 20 |

TEST EXAMPLE 10

A solution containing a sample compound in a predetermined concentration was coated by a paint brush in an amount of 110±10 mg on a rectangular parallelpiped wood block of Japanese red pine (20 mm×10 mm×10 mm). The treated wood block was naturally dried in a dark room of 25° C. for 14 days. Then, the treated wood block and a non-treated wood block were dried at a temperature of 60° C. for 72 hours, and their weights ($W_1$) were measured, and they were used as test specimens. Such a test specimen was put into a cylindrical cup made of acrylic resin (i.e. a cup having a hole with a diameter of 10 mm formed in the bottom and having hard plaster (Dental Stone) set at the bottom in a thickness of 10 mm), and 150 termite workers and 10 termite soldiers (*Reticulitermes speratus*) were released thereon. The cup was placed in a container having wet cotton laid over the bottom, and the container was maintained at room temperature of 25° C. for 24 days, whereupon the mortality of termites in the cup was examined. Further, the test specimen was taken out from the cup, and the deposited substance was removed from the surface of the test specimen. After drying at a temperature of 60° C. for 72 hours, it was weighed to obtain the weight ($W_2$), whereupon the mean weight loss was calculated. The results are shown in Table 10.

TABLE 10

| Sample compound | | Mortality (%) | | |
|---|---|---|---|---|
| | Concentration (%) | Termite workers | Termite soldiers | Mean weight loss (%) |
| Compound No. II-2 | 0.2 | 100 | 100 | 2.9 |
| No treatment | | 0 | 0 | 15.2 |

TEST EXAMPLE 11

1 g of powdered skim milk was treated with 1 ml of an acetone solution containing 10 mg of a sample compound and put in a constant temperature chamber at 40° C. for 20 hours to sufficiently evaporate acetone. In this manner, a poison bait chemical containing 1% of an active ingredient compound, was prepared. Then, this poison bait chemical was put into a cup together with a wet cotton, and 15 ants (*Lasius japonicus*) were released. 4 Days later, the mortality was examined. The results are shown in Table 11. Here, when the mortality 4 days later was at least 40%, the controlling effect was rated to be positive.

TABLE 11

| Sample compound | Bait concentration (%) | Controlling effect |
|---|---|---|
| Compound No. II-6 | 1 | Positive |
| No treatment | — | Negative |

TEST EXAMPLE 12

1 g of feeding stuff for mice was treated with 0.5 ml of an acetone solution containing 10 mg of a sample compound and put in a constant temperature chamber at 40° C. for 20 hours to sufficiently evaporate acetone, whereby a poison bait chemical containing 1% of the sample compound was prepared. Then, this poison bait chemical was put into a cup together with a wet cotton, and 10 ants (*Priplaneta americana*) were released and kept at 25° C. in a breeding room, whereby the mortality was examined as the time passed. The results are shown in Table 12.

TABLE 12

| | | Mortality (%) | | |
|---|---|---|---|---|
| Sample compound | Concentration (%) | 1 Day later | 8 Days later | 48 Days later |
| Compound No. II-2 | 1 | 0 | 0 | 30 |
| Compound No. II-3 | 1 | 0 | 100 | 100 |
| Chlorpyrifos | 1 | 100 | 100 | 100 |
| No treatment | — | 0 | 0 | 0 |

TEST EXAMPLE 13

A wood block of Japanese red pine (2 cm×2 cm×0.5 cm) subjected to boiling treatment in hot water, was immersed in a methanol solution of a sample compound, and then, it was dried to obtain a Japanese red pine poison bait chemical containing the sample compound in a predetermined concentration. This poison bait chemical was put into a cylindrical cup made of acrylic resin (i.e. a cup having a hole with a diameter of 10 mm formed in the bottom and having hard plaster (Dental Stone) set at the bottom in the thickness of 10 mm), and 15 termite workers (*Coptotermes formosanus*) were released thereon. The cup was placed in a container having wet cotton laid over the bottom, and the container was maintained at room temperature of 25° C., whereby the number of dead termites and abnormal termites in the cup was examined as the time passed, and the mortality was calculated. The results are shown in Table 13.

TABLE 13

| Sample compound | Concentration (%) | Mortality (abnormal ratio) (%) | | | | | |
|---|---|---|---|---|---|---|---|
| | | 4 Days later | 8 Days later | 10 Days later | 14 Days later | 17 Days later | 23 Days later |
| Compound No. II-2 | 0.1 | 73 | 100 | 100 | 100 | 100 | 100 |
| | 0.05 | 47 | 47 (14) | 80 (7) | 100 | 100 | 100 |
| | 0.01 | 0 | 40 (60) | 55 (45) | 60 (40) | 100 | 100 |
| | 0.005 | 0 | 0 | 0 | 30 | 30 (30) | 100 |
| No treatment | | 0 | 0 | 0 | 20 | 20 | 27 |

TEST EXAMPLE 14

A Japanese red pine poison bait chemical prepared in the same manner as in Test Example 13, was placed in a cylindrical cup made of acrylic resin (i.e. a cup having a hole with a diameter of 10 mm formed in the bottom and having hard plaster (Dental Stone) set at the bottom in a thickness of 10 mm), and 5 termite workers (*Coptotermes formosanus*) starved for 3 days, were released and permitted to ingest for 48 hours. Such bait-treated 5 alive termite workers were transferred together with non-treated 5 termite workers and 5 termite soldiers to a cup wherein a filter paper containing water was placed, and they were kept at room temperature of 25° C., whereby the number of dead termite workers and soldiers was examined as the time passed, and the mortality was calculated by the following formula. The results are shown in Table 14.

Mortality of workers (%)=(number of dead termite workers/treated 5 termite workers+non-treated 5 termite workers)×100

Mortality of soldiers (%) (number of dead termite soldiers/non-treated 5 termite soldiers)×100

TABLE 14

| Sample compound | Concentration (%) | Mortality (%) | | | | | |
|---|---|---|---|---|---|---|---|
| | | 6 Days later | | 8 Days later | | 15 Days later | |
| | | TW | TS | TW | TS | TW | TS |
| Compound No. II-2 | 0.1 | 50 | 0 | 60 | 20 | 100 | 100 |
| | 0.05 | 30 | 0 | 30 | 0 | 70 | 40 |
| No treatment | | 0 | 0 | 0 | 0 | 0 | 0 |

TW: Termite workers,
TS: Termite soldiers

TEST EXAMPLE 15

Fresh pulp (2 cm×2 cm×0.1 cm) was immersed in a methanol solution of a sample compound. Then, it was dried to obtain a fresh pulp poison bait chemical containing 0.1% of the sample compound. This poison bait chemical was placed in a cylindrical cup made of acrylic resin (i.e. a cup having a hole with a diameter of 10 mm formed in the bottom and having hard plaster (Dental Stone) set at the bottom in a thickness of 10 mm), and 20 termite workers (*Reticulitermes speratus*) were released thereon. The cup was placed in a container having wet cotton laid over the bottom, and the container was maintained at room temperature of 25° C. for 18 days, whereupon the number of dead termites in the cup was examined, and the mortality was calculated. The results are shown in Table 15.

TABLE 15

| Sample compound | Concentration (%) | Mortality (%) |
|---|---|---|
| Compound No. II-2 | 0.1 | 100 |
| No treatment | | 0 |

TEST EXAMPLE 16

A test was carried out in the same manner as the above Test Example 15 except that fresh pulp was changed to pulp (KIMUTAORU, tradename, manufactured by CRECIA Co.). The results are shown in Table 16.

TABLE 16

| Sample compound | Concentration (%) | Mortality (%) |
|---|---|---|
| Compound No. II-2 | 0.1 | 100 |
| No treatment | | 0 |

TEST EXAMPLE 17

Soil was packed in a cylindrical connection section made of an acrylic resin connecting two cups made of acrylic resin (i.e. cups each having a hole with a diameter of 10 mm formed in the bottom and having hard plaster (Dental Stone) set at the bottom in a thickness of 10 mm), and 30 termite workers and 3 termite soldiers (*Coptotermes formosanus*) were released to let them form an ant trail. Then, at the center portion of the ant trail, 10 mg of a dust prepared by mixing in a mortar 0.5 part by weight of a sample compound and 99.5 parts by weight of cellulose powder, was placed. This test apparatus was put into a container having wet cotton laid over the bottom and kept at room temperature of 25° C., whereby the number of dead termites in the cup was examined as the time passed, and the mortality was calculated. Further, for the purpose of comparison, a similar test was carried out with respect to a dust containing 0.5% of fipronil (Terminal Dust, tradename, manufactured by Aventis Crop Science Shionogi K.K.). These results are shown in Table 17.

TABLE 17

| Sample compound | Concentration (%) | Mortality (%) 6 Days later | 11 Days later | 15 Days later |
|---|---|---|---|---|
| Compound No. II-2 | 0.5 | 37 | 100 | 100 |
| Terminal Dust | 0.5 | 47 | 100 | 100 |
| No treatment | | 0 | 0 | 0 |

TEST EXAMPLE 18

1 mg of each dust prepared in the same manner as in Test Example 17, was uniformly dispersed in a small size glass Petri dish with a diameter of 45 mm, and 15 termite workers (*Coptotermes formosanus*) were released and treated for dust coating. The treated termite workers were put into a cylindrical cup made of acrylic resin (i.e. a cup having a hole with a diameter of 10 mm formed in the bottom and having hard plaster (Dental Stone) set at the bottom in a thickness of 10 mm) containing a bait log, together with 10 non-treated termite workers and 10 non-treated termite soldiers. The cup was placed in a container having wet cotton laid over the bottom, and the container was maintained at room temperature of 25° C., whereby the number of dead termites in the cup was examined as the time passed, and the mortality was calculated by the following formula. The results are shown in Table 18.

Mortality of termite workers (%)=(Number of dead termite workers/15 treated termite workers+10 non-treated termite workers)×100

Mortality of termite soldiers (%) (Number of dead termite soldiers/10 non-treated termite soldiers)×100

TABLE 18

| Sample compound | Concentration (%) | Mortality (%) | | | | | | |
|---|---|---|---|---|---|---|---|---|
| | | 1 Day later | | 8 Days later | | 15 Days later | | 19 Days later | |
| | | TW | TS | TW | TS | TW | TS | TW | TS |
| Compound No. II-2 | 0.5 | 0 | 0 | 4 | 0 | 52 | 40 | 100 | 100 |
| Terminal Dust | 0.5 | 100 | 10 | 100 | 100 | 100 | 100 | 100 | 100 |
| No treatment | | 0 | 0 | 0 | 0 | 0 | 0 | 0 | 0 |

TW: Termite workers,
TS: Termite soldiers

TEST EXAMPLE 19

A gel prepared by uniformity mixing 0.2 part by weight of potassium solvate, 20 parts by weight of sorbitol, 3.5 parts by weight of cross-linked product of a starch/sodium acrylate copolymer, a predetermined amount of a sample compound and a predetermined amount of water, was coated in an amount of 110 g/m² on a dried rectangular parallelpiped wood block of Japanese red pine of 20 mm (L)×10 mm (R)×10 mm (T). This test specimen was put into a cylindrical cup made of acrylic resin (i.e. a cup having a hole with a diameter of 10 mm in the bottom and having hard plaster (Dental Stone) set at the bottom in a thickness of 10 mm), and 20 termite workers (*Coptotermes formosanus*) were released thereon. The cup was placed in a container having wet cotton laid over the bottom, and the container was maintained at room temperature of 25° C., whereby the number of dead termites in the cup was examined as the time passed, and the mortality was calculated. The results are shown in Table 19.

TABLE 19

| Sample compound | Concentration (%) | Mortality (%) | | | | |
|---|---|---|---|---|---|---|
| | | 2 Days later | 6 Days later | 12 Days later | 23 Days later | 34 Days later |
| Compound No. II-2 | 0.1 | 0 | 60 | 100 | 100 | 100 |
| | 0.05 | 0 | 0 | 100 | 100 | 100 |
| | 0.01 | 0 | 0 | 10 | 60 | 100 |
| | 0.005 | 0 | 0 | 10 | 30 | 60 |
| No treatment | | 0 | 0 | 0 | 0 | 10 |

TEST EXAMPLE 20

Sandy soil passed through a sieve of 20 mesh, was dried at a temperature of 60° C. to a constant weight, and 4 g of the soil thus obtained, was packed into a cup having a diameter of 60 mm. 1 ml of a pesticide solution adjusted to a predetermined concentration was added and thoroughly mixed, whereupon 15 termite workers (*Coptotermes formosanus*) were leased. The cup was placed in a container having wet cotton laid over the bottom, and the container was maintained at room temperature of 25° C., whereby the number of dead termites in the cup was examined as the time passed, and the mortality was calculated. The results are shown in Table 20.

TABLE 20

| Sample compound | Concentration (ppm) | Mortality (abnormal ratio) (%) | | |
|---|---|---|---|---|
| | | 1 Day later | 4 Days later | 11 Days later |
| Compound No. II-2 | 4000 | 0 (100) | 100 | 100 |
| | 1000 | 0 | 73 (27) | 100 |
| | 250 | 0 | 0 (7) | 100 |
| No treatment | — | 0 | 0 | 0 |

TEST EXAMPLE 21

Sandy soil passed through a sieve of 20 mesh was dried at a temperature of 60° C. to a constant weight, and 12 g of the soil thus obtained, was packed into a cup having a diameter of 60 mm. 3 ml of a pesticide solution adjusted to a predetermined concentration, was added and sufficiently mixed, whereupon it was maintained in a constant temperature chamber of 40° C. for 95 days to carry out the weather resistance operation. After the weather resistance operation, 10 termite workers (*Reticulitermes speratus*) were released on this test soil. The cup was placed in a container having wet cotton laid over the bottom, and the container was maintained at room temperature of 25° C. 2 Days later and 6 days later after releasing the termites, the number of dead termites in the cup was examined, and the mortality was calculated. The results are shown in Table 21.

TABLE 21

| Sample compound | Concentration (ppm) | weather resistance operation | Mortality (abnormal ratio) (%) 2 Days later | 6 Days later |
|---|---|---|---|---|
| Compound No. II-2 | 1000 | Negative | 50 (50) | 100 |
|  |  | Positive | 10 (15) | 95 |
| No treatment | — |  | 0 | 25 |

TEST EXAMPLE 22

10 Ants (Lasius japonicus) were put into a test tube together with a cotton ball impregnated with 0.5 ml of a solution containing a sample compound in a predetermined concentration and containing 10% of cane sugar. 11 Days later, the number of dead ants was examined, and the mortality was calculated. The results are shown in Table 22.

TABLE 22

| Sample compound | Concentration (ppm) | Mortality (abnormal ratio) (%) 1 Day later | 2 Days later | 3 Days later | 8 Days later | 11 Days later |
|---|---|---|---|---|---|---|
| Compound No. II-2 | 50 | 30 (70) | 100 | 100 | 100 | 100 |
|  | 10 | 0 | 0 (20) | 40 | 80 | 100 |
| No treatment |  | 0 | 0 | 0 | 0 | 0 |

TEST EXAMPLE 23

A poison bait chemical containing a sample compound in an amount of 0.2% (W/W) was prepared by using, as a bait base material, skim milk to which (*Lasius japonicus*) showed preference. 2 g of this poison bait chemical was placed directly on an optional ground surface distanced by about 50 cm from the gate of the ant nest. Before, 2 days after, 3 days after and 5 days after placing the poison bait chemical, the number of ants going out and coming in through the gate per minute was examined. The results are shown in Table 23.

TABLE 23

| Sample compound | Number of ants in the habitat Before placing poison bait chemical | 2 Days later | 3 Days later | 5 Days later |
|---|---|---|---|---|
| Compound No. II-2 | 153 | 11 | 3 | 0 |
| No treatment | 25 | 22 | 24 | 21 |

TEST EXAMPLE 24

A filter paper having a diameter of 80 mm was placed in a plastic Petri dish, and 1 ml of a pesticide solution having a predetermined concentration was dropped thereon, whereupon 10 termite workers (*Coptotermes formosanus*) were released, and a cover was put on the Petri dish. This plastic Petri dish was put in a container having wet cotton laid over the bottom and maintained at room temperature of 25° C. On 21 or 28th day after the treatment, the number of dead termites in the Petri dish was examined, and the mortality was calculated in the same manner as Test Example 1. The results are shown in Tables 24, 25 and 26.

TABLE 24

(on 21st day after the treatment)

| Compound No. I-1 | Bifenthrin Mortality (theoretical value) (%) 1 ppm | 0.5 ppm | 0.25 ppm | 0 ppm |
|---|---|---|---|---|
| 200 ppm | 90 (52) | 80 (28) | 60 (20) | 20 |
| 100 ppm | 70 (52) | 60 (28) | 30 (20) | 20 |
| 50 ppm | 70 (40) | 40 (10) | 10 (0) | 0 |
| 0 ppm | 40 | 10 | 0 | 0 |

TABLE 25

(on 21st day after the treatment)

| Compound No. II-2 | Bifenthrin Mortality (theoretical value) (%) 1 ppm | 0.5 ppm | 0.25 ppm | 0 ppm |
|---|---|---|---|---|
| 20 ppm | 90 (76) | 90 (64) | 80 (60) | 60 |
| 10 ppm | 90 (52) | 70 (28) | 30 (20) | 20 |
| 5 ppm | 70 (40) | 40 (10) | 10 (0) | 0 |
| 0 ppm | 40 | 10 | 0 | 0 |

TABLE 26

(on 28th day after the treatment)

| Chlorfluazuron | Bifenthrin Mortality (theoretical value) (%) 1 ppm | 0.5 ppm | 0.25 ppm | 0 ppm |
|---|---|---|---|---|
| 2,000 ppm | 70 (58) | 70 (37) | 40 (30) | 30 |
| 1,000 ppm | 70 (58) | 60 (37) | 40 (30) | 30 |
| 500 ppm | 50 | 50 (28) | 30 (20) | 20 |
| 0 ppm | 40 | 10 | 0 | 0 |

INDUSTRIAL APPLICABILITY

According to the present invention, the composition comprising at least two compounds selected from the group consisting of a specific pyridine compound, a benzoylurea compound, a pyrethroid compound and a specific hydrazone compound, as active ingredients, can be used as an agent for controlling house insect pests such as termites or ants.

Also according to the present invention, the composition comprising a specific hydrazone compound as an active ingredient, can be used as an agent for controlling house insect pests such as termites or ants.

The invention claimed is:

1. A composition for controlling termites, comprising
   (i) Chlorfluazuron and
   (ii) Bifenthrin.

2. A method of controlling termites, comprising applying the composition of claim 1 to a termite habitat.

3. The method of claim 2, wherein the composition is applied to termites.

4. The method of claim 2, wherein the composition is fed to termites.

5. The method of claim 2, wherein the composition is applied to an ant trail.

6. The method of claim 2, wherein the composition is applied to an area damaged by termites.

7. The method of claim 2, wherein the composition is applied in baiting system.

* * * * *